United States Patent [19]

Zimmerman et al.

[11] Patent Number: 5,362,383

[45] Date of Patent: Nov. 8, 1994

[54] SELF-CONTAINED REVERSE OSMOSIS ELECTRONIC MONITORING SYSTEM

[75] Inventors: Jeffrey A. Zimmerman, Blaine; Marlin A. Frank, Minneapolis, both of Minn.

[73] Assignee: Ecowater Systems, Inc., Woodbury, Minn.

[21] Appl. No.: 3,758

[22] Filed: Jan. 13, 1993

[51] Int. Cl.⁵ .............................................. B01D 65/10
[52] U.S. Cl. ................................... 210/85; 210/96.1; 210/96.2; 324/439; 324/450
[58] Field of Search ........................ 210/85, 96.1, 96.2, 210/257.2, 232; 324/439, 446, 450; 340/603

[56] References Cited

U.S. PATENT DOCUMENTS

| | | | |
|---|---|---|---|
| 3,838,774 | 10/1974 | Dolan et al. | 210/85 |
| 4,204,956 | 5/1980 | Flatow | 210/87 |
| 4,623,451 | 11/1986 | Oliver | 210/87 |
| 4,744,895 | 5/1988 | Gales et al. | 210/96.2 |
| 4,762,611 | 8/1988 | Schipper | 210/96.2 |
| 4,925,551 | 5/1990 | Lipshultz | 210/140 |
| 4,937,557 | 6/1990 | Tucci et al. | 210/962 |
| 5,147,533 | 9/1992 | Lipshultz et al. | 210/257.2 |
| 5,281,330 | 1/1994 | Oikawa et al. | 210/85 |

Primary Examiner—Joseph W. Drodge
Attorney, Agent, or Firm—Jon Carl Gealow; James M. Wetzel

[57] ABSTRACT

A self-contained monitoring system for monitoring the operating condition of a fluid treatment device. A housing provides a pair of flow passages, one for liquid supplied to, and the other for liquid treated by the fluid treatment device. Separate pairs of electrodes are provided, with one pair of electrodes extending into one of the flow passages and the other pair extending into the other flow passage. The conductivities between each pair of electrodes are provided as signals to an electronic circuit contained within the housing which provides electrical output signals indicative of the operating condition of the fluid treatment device based upon the conductivity of the supplied and treated fluid flows.

10 Claims, 1 Drawing Sheet

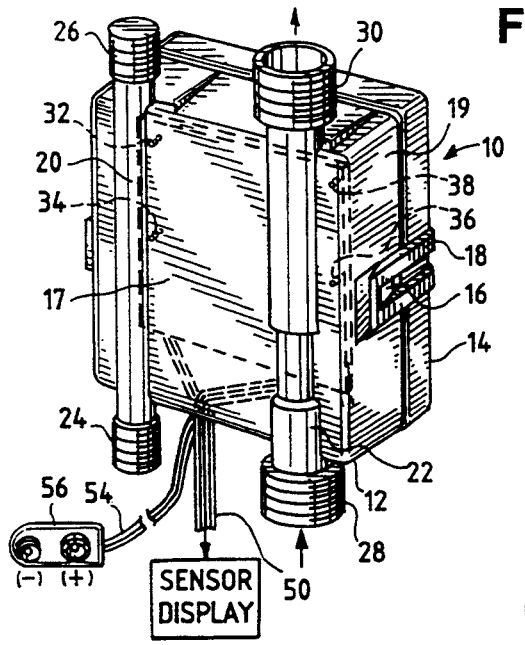
Fig. 1
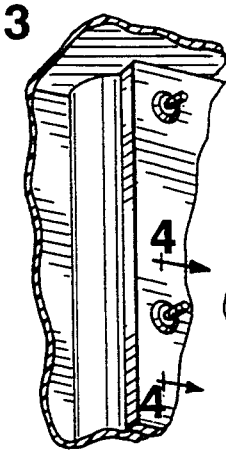
Fig. 3
Fig. 4
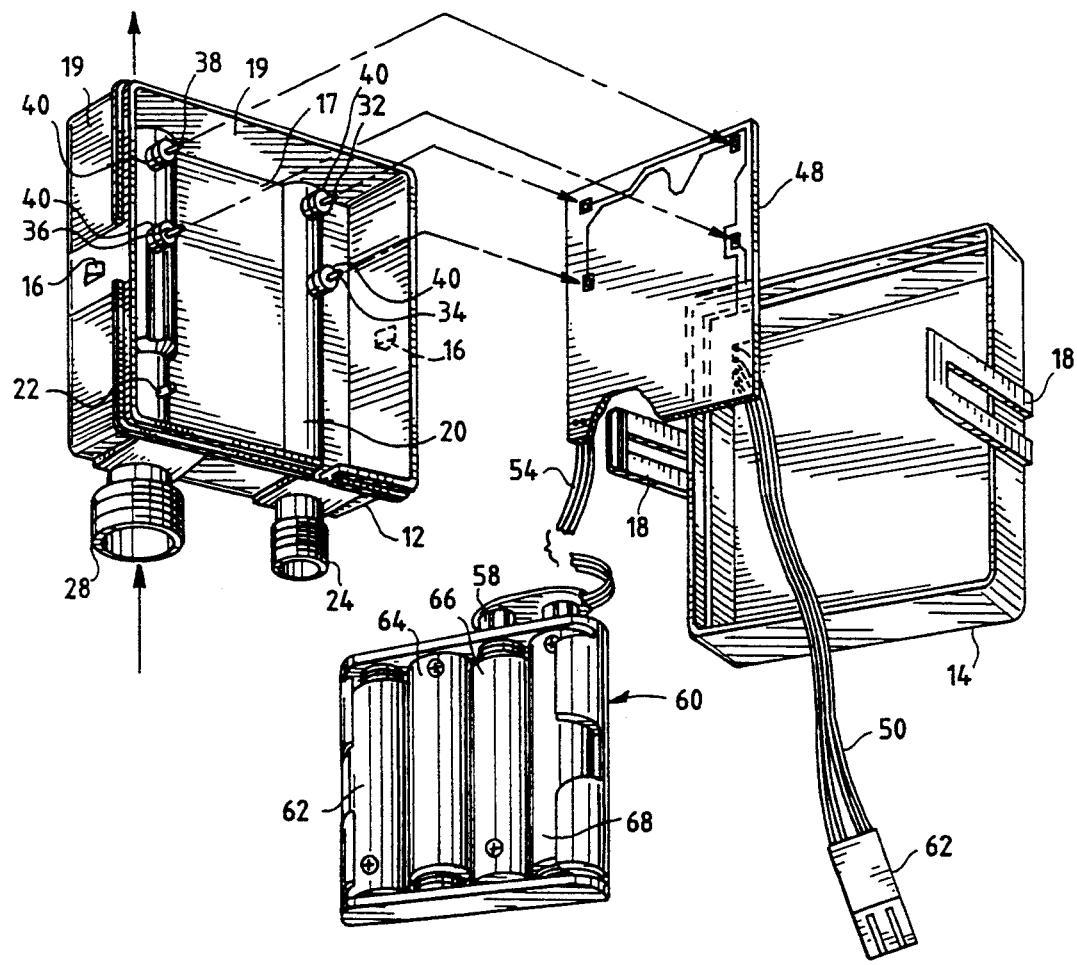
Fig. 2

SELF-CONTAINED REVERSE OSMOSIS ELECTRONIC MONITORING SYSTEM

BACKGROUND OF THE INVENTION

The effectiveness of a reverse osmosis water purification device can be monitored by a system which compares the conductivity of raw water supplied to the reverse osmosis device to the conductivity of treated water which has been passed through the reverse osmosis device. Such monitoring systems typically require the installation of two pairs of electronic probes, one pair is located in the flow, and spaced apart in the direction of flow of raw water to the reverse osmosis device and a second pair is located in the flow, and spaced apart in the direction of flow of processed or product water which has passed through the reverse osmosis device. The two pairs of electrodes are connected to an electronic circuit which is designed to compare the conductivities of the water flowing between the two pairs of electrodes and to provide an electrical output signal or signals to energize indicator lights or audible alarms which indicate the current operating condition of the reverse osmosis device. Further, it is necessary to provide a source of electrical power for the electronic circuit. As assembled in the past, such monitoring systems provided the two pairs of electrodes, the electronic circuit, and the source of electrical power as separate components, each of which was individually installed for use in monitoring a reverse osmosis water purification device.

SUMMARY OF THE INVENTION

It is an object of this invention to provide a self-contained monitoring system for monitoring the condition of a fluid treatment device such as a reverse osmosis water purification device and for providing electrical signals indicative of the current operating condition of the device. It is another object of this invention to provide a self-contained monitoring system which is readily assembled from a limited number of components. It is a further object of this invention to provide the self-contained monitoring system in a unitary package which is readily and conveniently installed for use with a reverse osmosis device.

In accordance with this invention, a housing is provided which includes elongated passages for carrying the flow of raw inlet and treated outlet water from a reverse osmosis device. Further, the housing supports and encloses two pair of electrodes, portions of one pair of which extend into the inlet water passage and portions of the other of which extend into the outlet water passage. The housing is also designed to support and enclose a printed circuit board. Electrically connected to the printed circuit board are the two pairs of electrodes, electrical leads on which appear electrical signals generated by the printed circuit indicative of the current operating condition of the reverse osmosis device, and electrical leads for connection to a source of electrical power. Space is also provided within the housing for an electrical power supply, such as dry cell batteries, for the electronic circuit.

In a preferred form of the self-contained electronic monitoring system of this invention, the printed circuit board is encapsulated in a potting compound after being connected to the electrodes, to leads extending to a connector which is connected to the electrical power supply, and to the leads providing electrical signals indicating the current operating condition of the reverse osmosis device. The electrical power supply includes a battery holder provided with a connector mating with that provided on the leads. A removable cover is provided for gaining access to the battery holder.

Other objects and further details of this invention will be set forth by making reference to the following drawings and specification.

IN THE DRAWINGS

FIG. 1 is a perspective view of the self-contained monitoring system of this invention.

FIG. 2 is an exploded perspective view showing the several components of the self-contained monitoring system of FIG. 1.

FIG. 3 is an enlarged partial perspective view of the self-contained monitoring system of FIG. 1 showing one of the pairs of electrodes.

FIG. 4 is a cross-sectional view of one of the electrodes taken along the line 4—4 in FIG. 3, showing its attachment to the housing and to the printed circuit board.

DETAILED DESCRIPTION

Referring to FIGS. 1 and 2, the self-contained electronic monitoring system for a reverse osmosis device of this invention is enclosed within a generally rectangular housing 10. The housing 10 consists of a base 12 and a cover 14. The cover 14 is secured to the base 12 by a hook and latch arrangement. Hooks 16 are provided on the base 12 and latches 18 are provided on the cover 14. The base 12 has a rectangular bottom 17 and sidewalls 19.

A pair of tubular passageways 20 and 22 are integrally formed in the base 12 to provide separate flow paths for unprocessed water entering a reverse osmosis device and for processed water discharged from a reverse osmosis device. As shown in FIGS. 1 and 2, the portions of the base forming the passageways 20 and 22 extend above and below the bottom 17. Externally threaded connectors 24 and 26 are provided at the ends of the tubular passageway 20 provided for the unprocessed or feed water. Similarly, external threads 28 and 30 are provided at the ends of the tubular passageway 22 provided for the processed water. The threaded connectors 24, 26, 28 and 30 extend outward beyond the sidewalls 19 of the base 12.

In a preferred embodiment of this invention, the externally threaded connectors 24, 26, 28 and 30 are of a standard type which may be readily threaded into female connectors provided at the ends of flexible plastic tubing which is used to connect the monitoring system to the reverse osmosis device, to a raw water supply, and to a processed water dispensing device. The pairs of externally threaded connectors 24 and 26, and 28 and 30 are formed with different diameters to aid in distinguishing the raw water and processed water passages. A source of unprocessed or feed water is connected to passageway 20 by a female connector secured to threaded connector 26. Feed water is supplied to the reverse osmosis device by a tubing connected to threaded connector 24. The processed water output of the reverse osmosis device is connected to threaded connector 28, and a dispensing device such as a faucet is connected to threaded connector 30.

As is best seen in FIGS. 2, 3 and 4, two pairs of electrodes 32 and 34 and 36 and 38 are mounted in the side walls of the tubular passageways 20 and 22 respectively. One end of each electrode projects into a passageway and the other end extends outwardly from the side walls of the passageway into the housing. Projecting cylindrical bosses 40, as shown in FIG. 4, are provided with cylindrical apertures 42 therein for receiving each of the electrodes 32, 34, 36 and 38. A water-tight seal is provided between the outer end of each of the bosses 40 and the electrode mounted therein. As shown in FIG. 4, rings 44 are secured such as by welding to the electrodes, and ring-like sealing means 46 are interposed between the outer end of the bosses 40 and the rings 44, to form the water-tight seals.

Referring to FIG. 2, a printed circuit board 48 is provided with an electronic circuit which receives and processes the water conductivity measurements made between the pairs of electrodes 32 and 34 and 36 and 38 and provides as an output electrical signals indicative of the current operating condition of the reverse osmosis device to electrical leads 50 which extend to a terminal block 52. Electrical leads 54 extend from the printed circuit board 48 to a connector 56 which is provided for connection with a mating connector 58 on a battery holder 60.

The printed circuit board is provided with holes which receive the outwardly extending portions of the electrodes 32 and 34, and 36 and 38 as shown in FIG. 4. After portions of the electrodes are extended through the holes in the printed circuit board 48, they are soldered thereto as shown in FIG. 4. Thus, secure mechanical and electrical connections are provided between the electrodes, the printed circuit board, and the circuit printed thereon. In a preferred embodiment, after the printed circuit board has been secured to the electrodes, the board is encapsulated in a potting compound. Sufficient potting compound is provided so as to cover the side of the board facing away from the base 12. Sufficient space is provided between the potting compound covering the printed circuit board and the top of the cover 14 so as to accommodate the battery holder 60. With batteries 62, 64, 66 and 68 placed in the battery holder, and the battery holder positioned over the printed circuit board, the cover 14 secured to the base 12 by engagement of the hooks 16 and the latches 18.

The self-contained electronic monitoring system is placed in use by connecting a plastic tubing supplying water to the reverse osmosis device to the threaded connector 26 and by connecting the threaded connector 24 to tubing supplying water to the reverse osmosis device. Water processed by the reverse osmosis device is supplied by a plastic tubing to threaded connector 28, and threaded connector 30 is connected by a plastic tubing to a dispensing device for the treated water, such as a faucet.

A sensor display shown as block 70 in FIG. 1 is connected to the connector 52. In a typical application, the sensor display may include a plurality of light emitting diodes incorporated in the base of the dispensing device, such as a faucet provided for dispensing the treated water. Particular patterns of lighted and unlighted light emitting diodes indicate the operating condition of the water treatment system.

Thus, in accordance with this invention, a self-contained electronic monitoring system is provided which is of simplified construction and which is readily connected to a liquid treatment system for monitoring the operating performance thereof.

It should be apparent to those skilled in the art that what has been described is considered at present to be the preferred embodiment of the self-contained electronic monitoring system of this invention. In accordance with the patent statutes, changes may be made in the electronic monitoring system without actually departing from the true spirit and scope of this invention. The appended claims are intended to cover all such changes and modifications which fall in the true spirit and scope of this invention.

We claim:

1. A monitoring system for a fluid treatment device comprising:

a housing comprising a base and a mating cover, a pair of elongated fluid flow passages integrally formed in said base, each of said fluid flow passages having an inlet and an outlet, fluid to be treated by the fluid treatment device flowing through a first one of said pair of elongated fluid flow passages, and the fluid treated by the fluid treatment device flowing said other one of said pair of elongated fluid flow passages, a first pair of electrodes, each of said electrodes of said first pair of electrodes each having a first portion extending into a first one of said elongated fluid flow passages, and a second portion extending into said housing, said first portions of said electrodes being spaced from each other such that one of said first portions is closer to said inlet and said other first portion is closer to said outlet of said first elongated fluid flow passage, a second pair of electrodes, each of said electrodes of said second pair of electrodes each having a first portion extending into a second one of said elongated fluid flow passages, and a second portion extending into said housing, said first portions of said electrodes being spaced from each other such that one of said first portions is closer to said inlet and said other first portion is closer to said outlet of said second elongated fluid flow passage, a printed circuit board located within said housing, a circuit printed on said printed circuit board being electrically connected to said second portions of said first and second pairs of electrodes such that said circuit derives inputs from said first and second pairs of electrodes representing the conductivity of the fluid flowing in the first and second elongated fluid flow passages between the first portions of the two pairs of electrodes, a power supply being located within said housing, said power supply being electrically connected to said printed circuit board, said circuit formed on said printed circuit board providing electrical output signals based upon the conductivity of the fluids flowing in the first and second elongated fluid flow passages between the respective first portions of the two pairs of electrodes, electrical leads connected to said printed circuit board and extending through said housing to provide said electrical output signals indicative of the operating condition of the fluid treatment device.

2. The monitoring system of claim 1, wherein said fluid flow passages are tubular, spaced from each other, and in a parallel relationship.

3. The monitoring system of claim 1, wherein said base has a rectangular bottom and has four edges and four sidewalls extending therefrom, said fluid flow passages being formed in said rectangular bottom, each of said inlets and outlets of said fluid flow passages having connecting portions extending beyond said edges of said base for connection to fluid conduits.

4. The monitoring system of claim 3, wherein portions of said housing base forming said flow passages project above and below said rectangular bottom of said base.

5. The monitoring system of claim 3, wherein said connecting portions of said passages extending beyond said edges of said base are externally threaded.

6. The monitoring system of claim 1, wherein said power supply comprises a battery holder and batteries.

7. The monitoring system of claim 6, wherein said battery holder is electrically connected to said printed circuit board through a pair of mating electrical connectors.

8. The monitoring system of claim 1, wherein said first and second pair of electrodes are secured to said base in a fluid tight manner, and are mechanically secured and electrically connected to said printed circuit board.

9. The monitoring system of claim 8, wherein portions of each of said electrodes extend into holes formed in said printed circuit board, which holes are surrounded by conductive members which are connected to said electrodes.

10. The monitoring system of claim 1, wherein said cover is removably secured to said base by at least one hook which is engaged by at least one clip.

* * * * *